US00PP32339P2

(12) United States Plant Patent
Stemkens

(10) Patent No.: US PP32,339 P2
(45) Date of Patent: Oct. 13, 2020

(54) ***HELENIUM* PLANT NAMED 'HEMZ0005'**

(50) Latin Name: *Helenium autumnale*
Varietal Denomination: HEMZ0005

(71) Applicant: SYNGENTA CROP PROTECTION AG, Basel (CH)

(72) Inventor: Henricus Godefridus Wilhelmus Stemkens, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/602,503

(22) Filed: Oct. 18, 2019

(30) Foreign Application Priority Data

Sep. 2, 2019 (QZ) ..... 2019/2113

(51) Int. Cl.
*A01H 5/02* (2018.01)
*A01H 6/14* (2018.01)

(52) U.S. Cl.
USPC ..... Plt./435

(58) Field of Classification Search
USPC ..... Plt./435
See application file for complete search history.

*Primary Examiner* — Susan McCormick Ewoldt
(74) *Attorney, Agent, or Firm* — Dale Skalla

(57) ABSTRACT

A new and distinct *Helenium* cultivar named 'HEMZ0005' particularly distinguished by a very compact plant habit and good branching. Flowers are single and bright red colored.

1 Drawing Sheet

Figure 1:
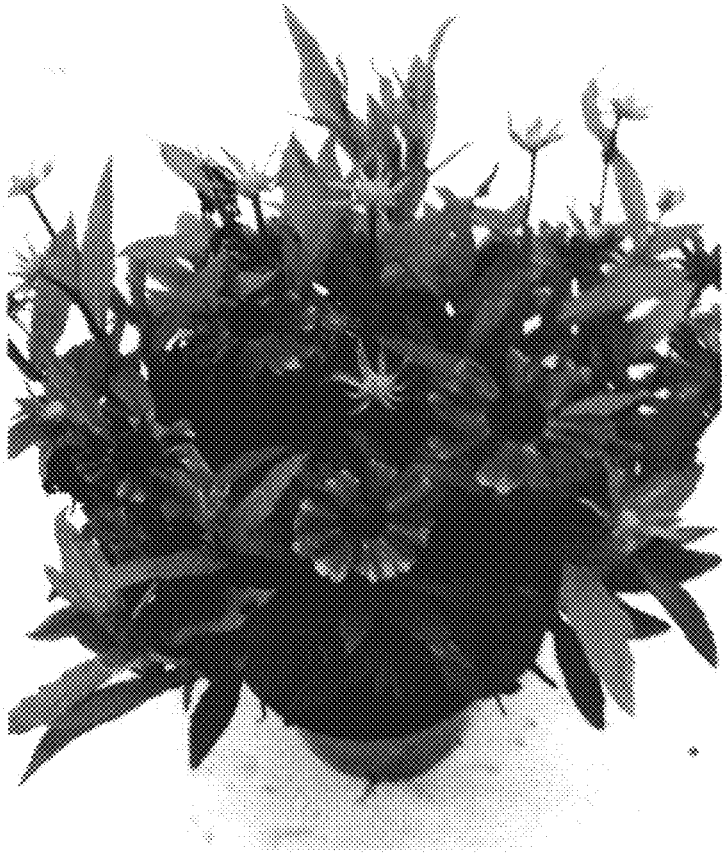

Latin name of the genus and species of the plant claimed: *Helenium autumnale.*

Varietal denomination: 'HEMZ0005'.

BACKGROUND OF THE NEW PLANT

The new *Helenium* cultivar is a product of a planned breeding program conducted by the inventor in Enkhuizen, The Netherlands. The objective of the breeding program was to produce new *Helenium* varieties. The open pollination resulting in this new variety was made during August of 2012.

The seed parent is the unpatented, propriety variety referred to as 'P6108-8'. The pollen parent is unknown and is a cloud of the total population of that year. The new variety was discovered in July of 2012 by the inventor in a group of seedlings resulting from the 2011 crossing, in an open field in Enkhuizen, The Netherlands.

Asexual reproduction of the new cultivar 'HEMZ0005' was first performed by terminal vegetative stem tip cuttings during September of 2012, at a greenhouse in in Enkhuizen, The Netherlands. Subsequent propagation by vegetative cuttings has shown that the unique features of this cultivar are stable and reproduced true to type in more than 20 successive generations.

BRIEF SUMMARY OF THE INVENTION

The cultivar 'HEMZ0005' has not been observed under all possible environmental conditions. The phenotype may vary somewhat with variations in environment such as temperature, day length, and light intensity, without, however, any variance in genotype.

A Plant Breeder's Right for this cultivar was applied for in the European Union on Sep. 3, 2019, No. 2019/2113. 'HEMZ0005' has not been made publicly available prior to the effective filing date of this application, notwithstanding any disclosure that may have been made less than one year prior to the effective filing date of this application by the inventor or another who obtained 'HEMZ0005' directly from the inventor.

The following traits have been repeatedly observed and are determined to be the unique characteristics of 'HEMZ0005'. These characteristics in combination distinguish 'HEMZ0005' as a new and distinct *Helenium* cultivar: 1. Distinctive bright red flower color 2. Very compact plant habit. 3. Uniform radial plant shape. 4. Full, dense plant.

PARENT COMPARISON

Plants of the new cultivar 'HEMZ0005' are similar to plants of the female seed parent, most horticultural characteristics, however, plants of the new cultivar 'HEMZ0005' differ in the following; 1. Plant habit of the new variety is more compact and round. The female seed parent is a more upright plant. 2. 'HEMZ0005' is shorter than the female seed parent. 3. 'HEMZ0005' has shorter peduncles than the female seed parent. 4. 'HEMZ0005' has larger flowers than the female seed parent.

COMMERCIAL COMPARISON

Plants of the new cultivar 'HEMZ0005' can be compared to the commercial variety 'Ranchera', U.S. Pat. No. 27,415. These varieties are similar in most horticultural characteristics; however, 'HEMZ0005' differs in the following: 1. 'HEMZ0005' has darker red color than 'Ranchera'. 2. 'HEMZ0005' is 20 cm shorter than 'Ranchera'. 3. Leaves of the new variety are smaller than 'Ranchera'.

BRIEF DESCRIPTION OF THE PHOTOGRAPHS

The accompanying photograph in FIG. 1 illustrates in full color a typical plant of 'HEMZ0005' grown in 13 cm pots outdoors in Enkhuizen, The Netherlands.

Figure 2:
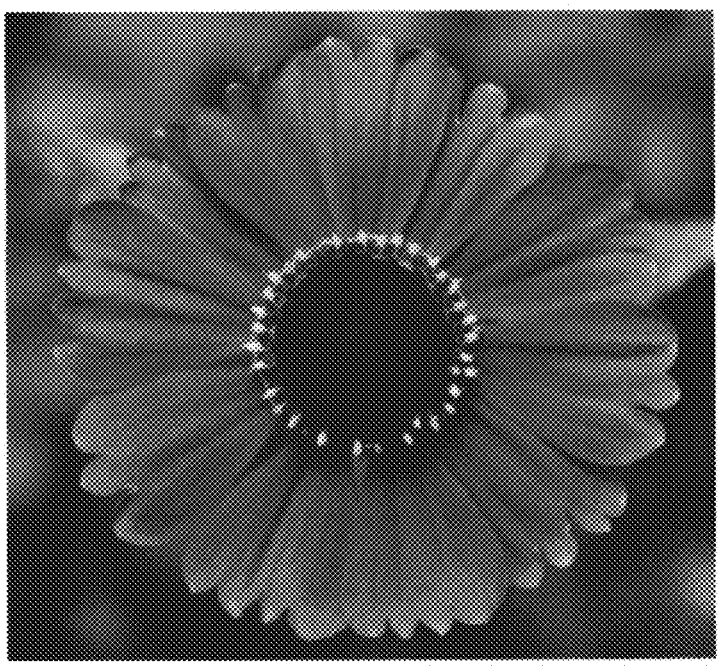

FIG. 2 illustrates in full color multiple typical inflorescence of 'HEMZ0005'. Age of the plant photographed is approximately 10 weeks from a rooted cutting in a 13 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'HEMZ0005' plants grown in a greenhouse in Enkhuizen, The Netherlands, under natural lighting. Measurements were taken during April of 2019. The plants were approximately 10 weeks old from a rooted cutting in a 13 cm pot. Measurements and numerical values represent averages of typical plant types.

Botanical classification: *Helenium autumnale* 'HEMZ0005'.

Propagation:

*Type cutting*.—Terminal stem.
*Time to initiate rooting*.—
*Summer*.—4 to 5 days at approximately 25 degrees C.
*Winter*.—5 to 6 days at approximately 25 degrees C.
*Total rooting time*.—About 15 days at approximately 25 degrees C. for a fully rooted cutting.
*Root description*.—Well branched. Fleshy and white, color RHS 155B.
*Rooting habit*.—Freely branching, dense.

Plant:

*Growth habit*.—Upright. Herbaceous perennial, vernalization not required for flowering.
*Hardiness*.—Zone 4a.
*Height*.—Approximately 22-26 cm.
*Plant spread*.—Approximately 12 cm.
*Growth rate*.—Moderate.
*Branching characteristics*.—Well branched, basal branching.
*Number of branches*.—12.
*Shape of lateral branches*.—Round with ridges from excurrent leaves.
*Length of lateral branches*.—Approximately 10 cm.
*Diameter of lateral branches*.—Approximately 0.4 cm.
*Texture of lateral branches*.—Glossy with very light and delicate hair, slightly ribbed longwise.
*Internodes length*.—Approximately 3.2 cm.
*Strength of stem*.—Flexible and strong, not likely to break.
*Color of lateral branches*.—RHS 144A.
*Aspect/angle of branches*.—Straight, occurring at approximately 45 degrees from ground level.
*Number of leaves per lateral branch*.—Approximately 12.

Foliage:

*Leaf*.—
*Form*.—Single.
*Arrangement*.—Alternate.
*Average length*.—Approximately 4-5 cm.
*Average width*.—Approximately 1.3 cm.
*Shape of blade*.—Oblanceolate.
*Apex*.—Acute.
*Base*.—Excurrent to stem.
*Attachment*.—Petiolate.
*Margin*.—Shallowly serrate.
*Texture of top surface*.—Very light and delicate hair.
*Texture of bottom surface*.—Very light and delicate hair.
*Color*.—
*Young foliage upper side*.—RHS 137B.
*Young foliage under side*.—RHS 147C.
*Mature foliage upper side*.—RHS 137C.
*Mature foliage under side*.—RHS 148B.
*Venation*.—
*Type*.—Pinnate.
*Venation color upper side*.—RHS N137B.
*Venation color under side*.—RHS N137C.
*Petiole*.—
*Length*.—2.3 cm.
*Diameter*.—0.2 cm.
*Pubescence*.—Very light and delicate hair.
*Color*.—RHS 144A.

Flower:

*Bloom period*.—Blooming occurs from early Summer to late Fall.
*Bud*.—
*Bud shape*.—Oblate.
*Bud length*.—Approximately 0.5 cm.
*Bud diameter*.—Approximately 1 cm.
*Bud color*.—RHS 147A.
*Inflorescence*.—
*Form*.—Composite, single.
*Lastingness*.—Individual flowers last approximately 12 to 20 days, depending on environmental conditions.
*Flower*.—
*Diameter of entire flower*.—Approximately 3.5 cm.
*Depth of flower*.—Approximately 1.5 cm.
*Diameter of disc*.—Approximately 1.1 cm.
*Depth of disc*.—Approximately 0.6 cm.
*Ray florets*.—
*Number of ray florets*.—Approximately 14.
*Average length*.—Approximately 1.3 cm.
*Width*.—Approximately 1.1 cm.
*Apex shape*.—Obdeltoid.
*Margin*.—Entire.
*Color*.—
*Ray florets*.—
*Upper surface at first opening*.—RHS N34A.
*Upper surface at maturity*.—RHS N34A.
*Upper surface at fading*.—RHS 166A.
*Under surface at first opening*.—RHS 183D.
*Under surface at maturity*.—RHS N34B.
*Under surface at fading*.—RHS 166A.
*Disc florets*.—
*Number of disc florets*.—Approximately 88.
*Length*.—Approximately 0.6 cm.
*Width*.—Approximately 0.2 cm.
*Shape*.—Tubular with 5 lobes on tip.
*Margin*.—Entire.
*Color*.—
*At first opening*.—RHS N144A.
*At maturity*.—RHS N186A.
*At fading*.—RHS N186A.
*Fragrance*.—None.
*Outer/involucral bracts*.—
*Number*.—Approximately 11.
*Sepal length*.—Approximately 1.1 cm.
*Sepal width*.—Approximately 0.4 cm.

*Sepal texture*.—Ribbed longwise.
*Apex shape*.—Acute.
*Margin*.—Entire.
*Color*.—RHS 138C.
*Peduncle*.—
*Peduncle length*.—Approximately 4 cm.
*Peduncle diameter*.—Approximately 0.2 cm.
*Angle*.—Approximately 90 degree from center of whorl.
*Color*.—RHS 137B.
*Strength*.—Flexible.
*Peduncle texture*.—Glabrous, shiny.

Reproductive organs:
*Disc florets*.—
*Anthoecium*.—Present, androecium of 5 stamens, these fused by their anthers, surrounding the style.
*Stamens*.—Present, quantity of 5 per floret.
*Anther shape*.—Linear and flat.
*Anther length*.—Approximately 0.2 cm.
*Anther color*.—RHS 186D.
*Pollen quantity*.—Profuse.
*Gynoecium*.—Present, ovary inferior, gynoecium of two fused carpels.
*Pistil number*.—
*Pistil shape*.—Cylindrical oblong tube with two branched at tip.
*Pistil length*.—Approximately 0.5 cm.
*Style length*.—Approximately 0.25 cm.
*Style color*.—RHS 145D.
*Stigma shape*.—V shaped with two, curved downward, branched-at tip.
*Stigma color*.—RHS N25C.
*Ovary length*.—0.2 cm.
*Ovary color*.—RHS 149A.
*Ray florets*.—No reproductive structures present.

Other characteristics:
*Seeds and fruits*.—No seedset observed.
*Disease/pest resistance*.—Typical to known *Helenium* varieties. Neither resistance nor susceptibility to the normal diseases and pests of *Helenium* have been observed. Pests common to *Helenium* include Aphids and thrips. Typical diseases are *Botrytis* and *Pythium*.
*Temperature tolerance*.—To USDA Zone 4a.
*Other tolerance*.—Tolerant to hot, humid summer climates.

What is claimed is:

1. A new and distinct cultivar of *Helenium* plant named 'HEMZ0005' substantially as illustrated and described herein.

* * * * *